US00PP18669P2

(12) United States Plant Patent
Bradford

(10) Patent No.: US PP18,669 P2
(45) Date of Patent: Mar. 25, 2008

(54) INTERSPECIFIC TREE NAMED 'YELLOWSWEET X'

(50) Latin Name: ***Prunus* sp.**
Varietal Denomination: YELLOWSWEET X

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,893

(22) Filed: Dec. 7, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP8,498 P * 12/1993 Bradford
PP14,219 P2 * 10/2003 Bradford

* cited by examiner

*Primary Examiner*—Kent Bell
*Assistant Examiner*—S. B. McCormick-Ewoldt

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, interspecific, or plum that blooms during the early to mid season. The fruit matures under the ecological conditions described during mid August, with first picking on Aug. 19, 2006. The fruit is uniformly medium in size, yellow in skin color, clingstone in type, globose in shape, firm in texture, and mildly acidic and sweet in flavor.

1 Drawing Sheet

Botanical classification: *Prunus* sp.
Varietal denomination: 'YELLOWSWEET X'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'YELLOWSWEET X'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 1997 one such house containing 'BRADGREEN' (U.S. Plant Pat. No. 8,498) plum was crossed by me in this manner. To pollinate this plum, I selected bouquets from several sources of apricot and interspecific plum-apricot hybrid trees with keeping specific written details. Upon reaching maturity the fruit from this plum tree was harvested, and the seeds were removed, cracked, stratified and germinated as a group with the label "42PH10". They were grown as seedlings on their own root in my greenhouse and upon reaching dormancy transplanted to a cultivated area of my experimental orchard located near Le Grand, Calif. in Merced County (San Joaquin Valley). During the summer of 2000 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'BRADGREEN' (U.S. Plant Pat. No. 8,498) plum, by being self-unfruitful and by producing fruit that is large in size and sweet in flavor, but is distinguished therefrom by blooming about seven days later, by being more productive, and by producing fruit that is predominantly yellow instead of green in skin color and that matures about two weeks earlier.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the mid season, such as 'Plumsweetone' (U.S. Plant Pat. No. 14,219). The present variety's abundance of blossoms and pollen entices strong bee activity to facilitate pollination. The fruit matures under the ecological conditions described during mid August, with first picking on Aug. 19, 2006. The fruit is uniformly medium in size, yellow in skin color, clingstone in type, globose in shape, firm in texture, and mildly acidic and sweet in flavor.

DRAWING

The accompanying photograph consists of four whole fruits positioned to display the characteristics of the skin color and form, one fruit divided transversely to the suture plane to reveal the flesh and stone, typical leaves, and an inset displaying the blossoms as they appear on the tree.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Aug. 25, 2006, on the original tree during its ninth growing season. The flower and bud descriptions were developed during the previous blooming season. All major color code designations are by reference to the Inter-Society Color Council, National Bureau of Standards. Common color names are also used occasionally.

Parentage:
- *Seed parent.*—'Bradgreen' (U.S. Plant Pat. No. 8,498).
- *Pollen parent.*—Unknown.

Tree

Size: Medium, reaching and maintaining a height of 9' [2.74 m.] and a spread of 7' [2.13 m.] after nine growing seasons utilizing typical dormant pruning.

Vigor: Medium, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually required.

Fertility: Self-unfruitful, requiring cross pollination by a suitable early to mid seasonal blooming apricot, interspecific, or plum, such as 'Plumsweetone' (U.S. Plant Pat. No. 14,219).

Bearing: Reliable bearer, but dependent upon favorable weather during the blooming period.

Trunk:
- *Size.*—Medium, reaching a maximum diameter of 4" [102 mm.] after the ninth growing season.
- *Texture.*—Rough.
- *Bark color.*—A Brownish gray [64. brGy] and Deep brown [56. deep Br] variegation with Light yellowish brown [76. l.yBr] crevices present.
- *Lenticels.*—Approximate Number Per Square Inch: 15. Color: Deep orange yellow [69. deep OY]. Typical Size: 1/8" [3.2 mm.] to 7/16" [11.1 mm.]. Shape: Eye-shaped to elongated.

Branches:
- *Size.*—Diameter of limb is 2¼" [57 mm.] measured 12" above the crotch, 1⅛" [29 mm.] measured 12" above the first fork.
- *Texture.*—Smooth on first and second year wood, increasing roughness with age.
- *Color.*—1st Year Wood Topside: Light reddish brown [42. l.rBr]. 1st Year Wood Underside: Brilliant yellow green [116. brill.YG]. Older Wood: Deep yellowish brown [75. deep yBr].
- *Lenticels.*—Number Per Square Inch: More than 40 on second year wood. Color: Light yellowish brown [76. l.yBr]. Typical size: 1/64" [0.4 mm.] to 3/32" [2.4 mm.]. Shape: Elongated.

Leaves:
- *Size.*—Medium. Average Length: 4¼" [108 mm.]. Average width: 1 15/16" [49 mm.].
- *Arrangement.*—Alternate.
- *Thickness.*—Medium.
- *Form.*—Elliptical.
- *Apex.*—Acuminate.
- *Base.*—Acute with an average base angle of 70 to 80 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: 9/16" [14.3 mm.]. Average Thickness: 1/16" [1.6 mm.]. Color: Grayish red [19. gy.R] on the topside and Light yellow green [119. l.YG] on the underside.
- *Stipules.*—Number: 2 per leaf, up to 6 per growing tip. Average Length: ⅜" [9.5 mm.]. Color: Pale yellow green [121. p.YG] becoming Light reddish brown [42. l.rBr] with age.
- *Glands.*—Average Number: 4 per leaf. Position: Mostly alternate, some opposite, the first pair usually positioned on the petiole and the rest on the leaf blade. Size: Small. Form: Globose. Color: Light yellow green [119. l.YG] becoming Dark grayish reddish brown [47. d.gy.rBr] with age.
- *Leaf buds.*—Pointed, medium.

Flower buds:
- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Color.*—White [263. White].

Flowers: Perfect, complete, perigynous, usually a single pistil, typically thirty or more stamens, five sepals and petal locations alternately positioned.
- *Average flower diameter.*—1" [25.4 mm.].
- *Number of petals.*—Five, no double blossoms observed.
- *Petal shape.*—Circular to oval.
- *Petal margin.*—Smooth.
- *Average petal diameter.*—7/16" [11.1 mm.].
- *Average petal length.*—½" [12.7 mm.].
- *Petal apex.*—Rounded.
- *Petal base.*—Rounded to somewhat obtuse.
- *Petal color.*—White [263. White].
- *Anther color.*—Strong orange yellow [68. s.OY] in the center with a tinge of Moderate yellowish pink [29. m.yPk] on the surface.
- *Stigma color.*—Pale greenish yellow [104. p.gY].
- *Sepal color.*—Dark reddish orange [38. d.rO].
- *Sepal length.*—5/32" [4.0 mm.].
- *Sepal width.*—⅛" [3.2 mm.].
- *Average pistil length.*—9/16" [14.3 mm.].
- *Average stamen length.*—½" [12.7 mm.].
- *Fragrance.*—Moderate.
- *Pollen production.*—Moderate.

*Blooming period.*—Early to medium at the onset, starting about two days after 'Black Amber' (unpatented), but finishing much later.
*Onset of bloom.*—One percent on Feb. 15, 2006.
*Date of full bloom.*—Mar. 5, 2006.
*Duration of bloom.*—Seven to seventeen days, dependent on ambient temperature.
*Bloom density.*—Extremely heavy.
*Number per cluster.*—2 to 9, average 4.

FRUIT

Maturity when described: Full ripe, Aug. 25, 2006.
Date of first picking: Aug. 15, 2006.
Date of last picking: Aug. 25, 2006.
Size: Uniform, medium.
*Average diameter axially.*—2⅝" [67 mm.].
*Average diameter across cheek plane.*—2⅝" [67 mm.].
*Average diameter across suture plane.*—2⅝" [67 mm.].
*Typical weight.*—6.4 ounces [181 grams].
Form: Uniform, symmetrical, globose.
*Longitudinal section form.*—Round to elliptical.
*Axial view.*—Round.
Suture: An inconspicuous line in a shallow groove extending from the base to apex.
Ventral surface: Rounded, lipped slightly toward the base.
Lips: Equal.
Cavity: Flaring, circular to slightly elongated in the suture plane, suture showing on one side, no visible stem markings.
*Depth.*—7/16" [11.1 mm.].
*Breadth.*—15/16" [23.8 mm.].
Base: Truncate, slightly cordate if viewed parallel to suture.
Apex: Rounded with a slight hump just before the pistil point.
Pistil point: An inconspicuous dot.
Stem: Medium.
*Average length.*—7/16" [11.1 mm.].
*Average width.*—3/32" [2.4 mm.].
Skin:
*Thickness.*—Medium.
*Surface.*—Smooth.
*Tenacity.*—Tenacious to flesh.
*Taste.*—Astringent.
*Tendency to crack.*—Slight on the suture near the base.
*Color.*—Brilliant yellow [83. brill.Y] over a Brilliant greenish yellow [98. brill.gY] background.
*Bloom.*—Moderate.
Flesh:
*Color.*—Light yellow [86. l.Y] near the stone, Light greenish yellow [101 l.gY] near the skin.
*Surface of pit cavity.*—Moderate yellow [87. m.Y] broken fibers when twisted away from stone.
*Amygdalin.*—Moderate.
*Juice.*—Abundant, rich.
*Texture.*—Firm, meaty.
*Fibers.*—Abundant, fine.
*Ripens.*—A little earlier toward the apex.
*Flavor.*—Mildly acidic and sweet, typically 18 brix.
*Aroma.*—Very slight.
*Eating quality.*—Very good.

STONE

Type: Clingstone.
Form: Oval.
Hilum: Narrow, oblong.
Base: Straight.
Apex: Obtuse with an average angle of 110 degrees.
Sides: Equal.
Surface: Rough throughout, with a few small vertical ridges running from the base to mid section.
External color of stone: Light yellowish brown [76. l.yBr].
Pit wall color when cracked: Pale orange yellow [73. p.OY].
Cavity surface color: Deep yellowish brown [75. deep y.Br].
Average pit wall thickness: 1/16" [1.6 mm.].
Average width: 11/16" [17.5 mm.].
Average length: 15/16" [23.8 mm.].
Average breadth: ⅜" [9.5 mm.].
Tendency to split: Slight.
Kernel:
*Form.*—Oval.
*Skin color.*—Pale yellow [89. p.Y] when first removed.
*Pellicle color.*—Yellowish gray [93. yGy].
*Vein color.*—Light grayish brown [60. l.gy.Br].
*Taste.*—Bitter.
*Viable.*—Yes.
*Average width.*—7/16" [11.1 1 mm.].
*Average length.*—9/16" [14.3 mm.].
*Amygdalin.*—Abundant.

Use

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.
Resistance to heat: Some heat damage observed following extended period of temperatures in excess of 110 degrees Fahrenheit during the 2006 season, none observed during the 2005 season.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to its seed parent, 'BRADGREEN' (U.S. Plant Pat. No. 8,498) plum, by being self-unfruitful and by producing fruit that is medium in size and sweet in flavor, but is distinguished therefrom by blooming about seven days later, by being more productive, and by producing fruit that is predominantly yellow instead of green in skin color and that matures about two weeks earlier.

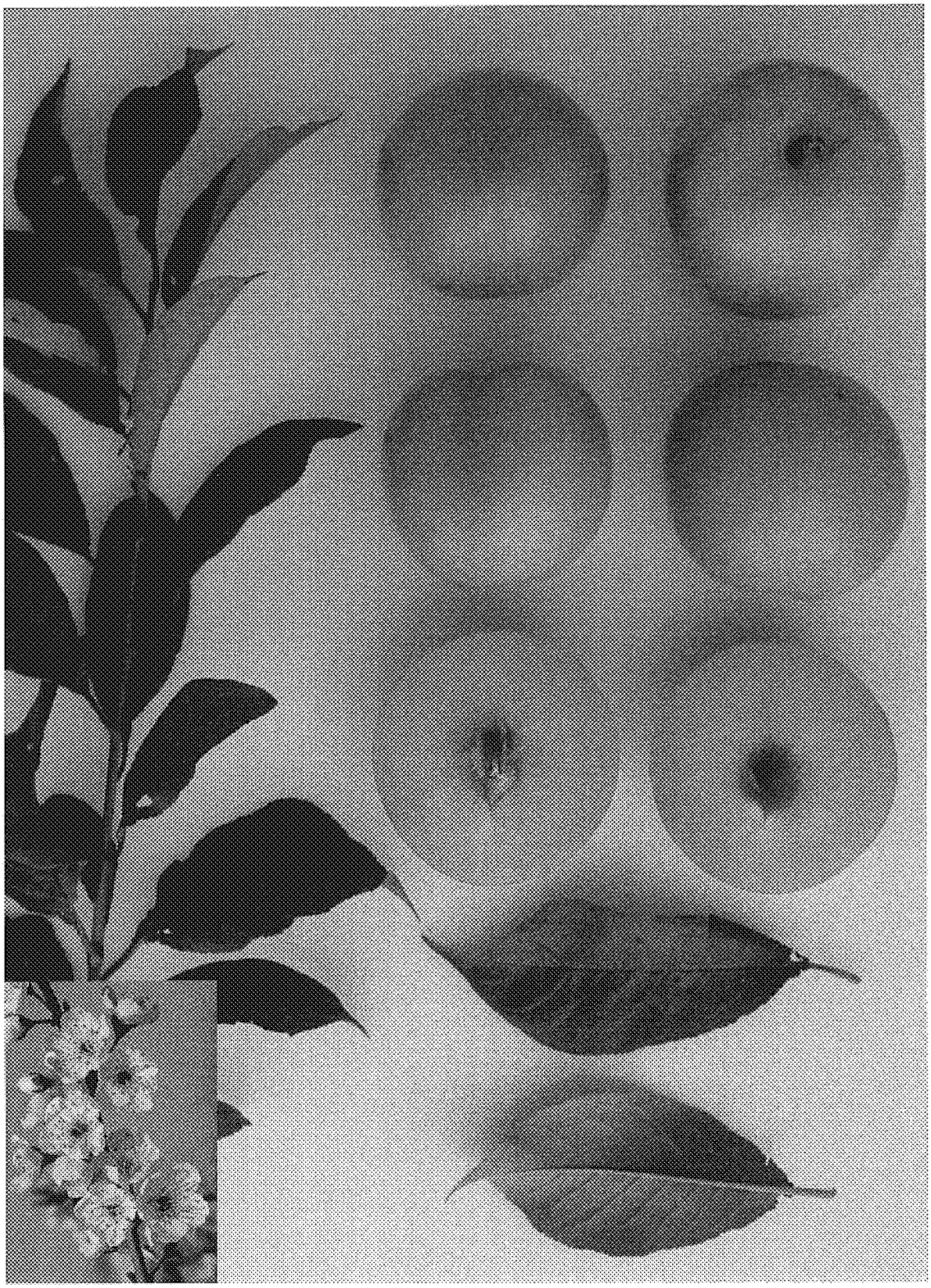

* * * * *